United States Patent
Dalton et al.

(10) Patent No.: US 9,145,448 B2
(45) Date of Patent: Sep. 29, 2015

(54) METHOD FOR THE ISOLATION OF HAPTOGLOBIN

(75) Inventors: Joan Dalton, Elstree (GB); Adrian Podmore, Elstree (GB); Peter Kumpalume, Elstree (GB)

(73) Assignee: BIO PRODUCTS LABORATORY LIMITED, Hertfordshire (GB)

( * ) Notice: Subject to any disclaimer, the term of this patent is extended or adjusted under 35 U.S.C. 154(b) by 1679 days.

(21) Appl. No.: 11/577,478

(22) PCT Filed: Oct. 19, 2005

(86) PCT No.: PCT/GB2005/004037
§ 371 (c)(1),
(2), (4) Date: Jul. 15, 2009

(87) PCT Pub. No.: WO2006/043062
PCT Pub. Date: Apr. 27, 2006

(65) Prior Publication Data
US 2009/0281282 A1 Nov. 12, 2009

(30) Foreign Application Priority Data
Oct. 19, 2004 (GB) .................................. 0423196.5

(51) Int. Cl.
*C07K 1/18* (2006.01)
*C07K 14/00* (2006.01)
*A61K 38/16* (2006.01)
*C07K 14/47* (2006.01)
*A61K 38/17* (2006.01)
*B01D 15/36* (2006.01)

(52) U.S. Cl.
CPC ............. *C07K 14/47* (2013.01); *A61K 38/1722* (2013.01); *B01D 15/363* (2013.01); *C07K 1/18* (2013.01); *C07K 14/4717* (2013.01)

(58) Field of Classification Search
None
See application file for complete search history.

(56) References Cited

U.S. PATENT DOCUMENTS

| 4,061,735 | A | | 12/1977 | Funakoshi et al. |
| 4,103,687 | A | | 8/1978 | Ishii |
| 4,137,307 | A | | 1/1979 | Funakoshi et al. |
| 5,094,960 | A | * | 3/1992 | Bonomo .................... 436/178 |
| 2003/0158391 | A1 | | 8/2003 | Hennies |
| 2005/0063951 | A1 | | 3/2005 | Moestrup et al. |

FOREIGN PATENT DOCUMENTS

| EP | 0131740 | | 1/1985 |
| EP | 0367220 | A2 | 5/1990 |
| GB | 1 426 039 | | 2/1976 |
| JP | 2004-244348 | | 9/2004 |
| JP | 2004-244348 | A | 9/2004 |
| WO | WO 03/006668 | A2 | 1/2003 |
| WO | WO 2006/043062 | A1 | 4/2006 |
| WO | WO 2006/107708 | A1 | 10/2006 |

OTHER PUBLICATIONS

Martin. 1949 J Am Chem Soc 71(4): 1230-1232.*
Piet et al. 1990 Transfusion 30(7): 591-598.*
Connell, G.E., et al. 1961 Can J Biochem Physiol 39: 1013-1019.*
Akaiwa, S. (1982) "Purification of haptoglobin from rat serum" Analytical Biochemistry 123:178-182.
Baseler, M.W. et al. (1983) "Purification of haptoglobin and its effects on lymphocyte and alveolar macrophage responses" Inflammation 7:387-400.
Chiancone, E. et al. (1995) "Preparative and analytical applications of immobilized haemoglobin" Journal of Chromatography B. 664:89-95.
Cohn, E.J. et al. (1946) "Preparation and properties of serum and plasma proteins. IV. A system for the separation into fractions of the protein and lipoprotein components of biological tissues and fluids" J. Am. Chem. Soc. 68:459-475.
Hansson, L-O. et al. (1998) "Typing of heptoglobin using PhastSystem" Application Note 373 for the PhastSystem, 4pp.
Katnik, I. et al. (1993) "Immunoaffinity purification of human haptoglobin using monoclonal antibodies" Archivum Immunologiae et Therapiae Experimentalis, 41:303-308.
Katnik, I. et al. (1995) "Measurements of haptoglobin by the reaction with concanavalin A in sera of patients with ovarian tumours" Eur. J. Clin. Chem. Clin. Biochem. 33:727-732.
Khoch, W. et al. (2002) "Genotyping of the common haptoglobin hp ½polymorphism based on pcr" Molecular Diagnostics and Genetics 48:1377-1382.
Kistler, P. et al. (1962) "Large scale production of human plasma fractions" Vox Sang. 7:414-424.
Liau, C. et al. (2003) "Purification of human plasma haptoglobin by hemoglobin-affinity column chromatography" Journal of Chromatography B 790:209-216.
Nayak, B. et al. (2002) "Selective precipitation of haptoglobin and α-2-macroglobulin from human serum using alocasia macrorhiza tuber protein" Protein and Peptide Letters 9:503-510.
Tseng, C. et al. (2004) "Purification of human haptoglobin 1-1, 2-1, and 2-2 using monoclonal antibody affinity chromatography" Protein Expression and Purification 33: 265-273.

(Continued)

*Primary Examiner* — Marsha Tsay
(74) *Attorney, Agent, or Firm* — Knobbe, Martens, Olson & Bear, LLP

(57) ABSTRACT

The invention provides a method for the isolation of haptoglobin from a sample comprising Cohn fraction V, wherein said method comprises anion exchange chromatography of said sample. The product may be further purified and/or subjected to one or more virus inactivation or reduction steps. The isolated haptoglobin may then be formulated for pharmaceutical use.

25 Claims, 6 Drawing Sheets

(56) References Cited

OTHER PUBLICATIONS

Yang, S. et al. (1999) "Simple high-performance liquid chromatographic purification procedure for porcine plasma haptoglobin" Journal of Chromatography B 731:395-402.

Cohn, E.J. et al. 1944 "Chemical, Clinical, and Immunological Studies on the Products of Human Plasma Fractionation. I. The Characterization of the Protein Fractions of Human Plasma" *J Clin Invest* 23(4): 417-432.

Platt 2000 "Sickle cell anemia as an inflammatory disease" *The Journal of Clinical Investigation* 106(3); 337-338.

Reiter, C.D. et al. 2002 "Cell-free hemoglobin limits nitric oxide bioavailability in sickle-cell disease" *Nature Medicine* 8(12):1383-1389.

Villa-Boas, et al. 2012 "Sickle cell disease: Only one road, but different pathways for inflammation" *Advances in Bioscience and Biotechnology* 3; 538-550.

\* cited by examiner

METHOD FOR THE ISOLATION OF HAPTOGLOBIN

RELATED APPLICATIONS

This application is a U.S. National Phase of International Application No.: PCT/GB2005/004037, filed Oct. 19, 2005, designating the U.S. and published in English as WO 2006/043062 on Apr. 27, 2006, which claims the benefit of British Application No.: 0423196.5, filed Oct. 19, 2004.

FIELD OF THE INVENTION

Haptoglobin (Hp) is an acute-phase response protein, synthesised mainly in the liver. It is also synthesised in other tissues such as arterial walls, endometrium and peritoneum.

BACKGROUND OF THE INVENTION

The core function of Hp is as a haemoglobin (Hb) binding protein, required for terminal processing and disposal of free Hb, mostly in the reticular endothelial system (RES) of the liver. This system allows the iron present in the Hb moiety to be conserved.

The haem (ferroprotoporphyrin DX) molecule found in Hb is an indispensable element in a wide variety of other protein systems (e.g. enzymes such as cyclooxygenase [COX] and nitric oxide synthase [NOS]), acting according to the properties of the polypeptide(s) bound to it. However, excess of free haem can cause cell damage and tissue injury (e.g. in kidney, lung and CNS) since it catalyses the formation of reactive oxygen species, which in turn cause oxidative stress.

Intravascular haemolysis occurs physiologically, but also accelerates as a severe complication in various autoimmune, infectious (e.g. malaria) and inherited (e.g. sickle cell) diseases. During haemolysis, free vascular Hb is captured by Hp and transported to the liver RES. Some processing may also take place in monocyte-macrophages. However, free vascular Hb can be rapidly converted to met-Hb, which readily liberates the potentially toxic haem moiety. Free vascular haem is captured by albumin or haemopexin (Hx) and is transported to the liver for degradation in the RES. When large amounts of haem accumulate (e.g. in a blood clot or vascular deposition), the scavenging mechanisms are overwhelmed or unable to gain access to the free haem, and tissue damage results. If the amount of red cell lysis saturates the haem/Hb removal system, Hb will start to appear in the urine (glomerular filtration by the kidney).

Hp has a tetrameric structure comprising two α and two β chains, linked by disulphide linkages. The β chain (245 amino acids) has a mass of about 40 kDa (of which approximately 30% w/w is carbohydrate) and is shared by all phenotypes. The α chain exists in two forms: α1, (83 amino acids, 9 kDa) and α2 (142 amino acids, 17.3 kDa) and therefore Hp occurs as three phenotypes, referred to as Hp1-1, Hp2-1 and Hp2-2. Hp1-1 contains two α1 chains, Hp2-2 contains two α2 chains, and Hp2-1 contains one α1 and one α2 chain. Hp 1-1 has a molecular mass of 100 kDa, or 165 kDa when complexed with Hb. Hp1-1 exists as a single isoform, and is also referred to as Hp dimer. Hp2-1 has an average molecular mass of 220 kDa and forms liner polymers. Hp2-2 has an average molecular mass of 400 kDa and forms cyclic polymers. Each different polymeric form is a different isoform. A PCR methodology has been devised (Koch et al. 2002, Clin. Chem. 48: 1377-1382) for studying Hp polymorphism.

Hp has been identified as a potential treatment for renal disorders caused by haemolysis. It is potentially useful therapeutically as a means of removing free haemoglobin; the complexes thus formed having potential additional benefits as anti-inflammatory, antioxidant or angiogenic agents. However, Hp is considered difficult to isolate in large amounts whilst retaining its biological activity. A variety of protocols for the isolation of Hp have been described. A common theme is affinity chromatography. Affinity ligands used include monoclonal antibodies (Katnik and Jadach, 1993, Arch. Immunol. Ther. Exp. (Warz) Vol 41: 303-308 and Tseng et al 2004, Protein Expr Purif 33: 265-273), haemoglobin (Liau et al. 2003, J. Chromatogr. Analyt, Technol Biomed Life Sci. 790: 209-216 and Chiancone et al. 1995, J. Chromatogr. Biomed. Appl. 664: 89-95) and concanavalin A (Katnik et al. 1995, Eur J. Clin. Chem. Clin. Biochem. 33:727-732).

Although monoclonal antibody based affinity ligand protocols result in reasonably pure product only low yields have been reported. Such methods of isolation are also not well suited to large-scale production processes as a result of the need for large amounts of affinity ligand. In particular, the required amounts of monoclonal antibodies are likely to be prohibitively expensive, and difficult to obtain. Monoclonal antibodies also suffer from the potential draw back of being selective for the various isoforms of Hp. Use of Hb as the affinity ligand has achieved more success. Good yields of reasonably homogenous Hp have been achieved, however, as with all affinity ligand based protocols, scaling up the process is difficult and often not cost effective. A further drawback of affinity ligand based protocols is that if the Hp product is destined for use as a pharmaceutical, the source of the affinity ligand must be controlled. In this regard, Hb may not be acceptable to regulators, since it is sourced from red blood cells. It is also necessary to monitor and control the leaching of the ligand, as the presence of the affinity ligand in the product may raise concern for its safe use in patients.

Selective precipitation of Hp by a plant root extract has also been described (Nayak et al 2002, Pro. Pep. Lett 9: 503-510). However, like affinity chromatography, this protocol is unsuited to large-scale commercial production.

HPLC (High Performance Liquid Chromatography) based techniques have also been performed on an ammonium sulphate precipitate of porcine serum (Yang and Mao, 1999, J. Chromatogr. B. Biomed. Sci. Appl., 731: 395-402). Again, this protocol is only considered suitable for small-scale isolation of Hp.

An alternative approach to the isolation of Hp has been to use ion exchange chromatography. U.S. Pat. No. 4,061,735 and U.S. Pat. No. 4,137,307 have described Hp isolation through anion exchange chromatography of ammonium sulphate precipitates of human plasma or Cohn fractions IV, IV-1 or IV-4 derived from human plasma. The ammonium sulphate precipitation is stated to remove transferrin, albumin and other undesirable proteins. It is essential for this method that the ion exchange substrate is a strong anion exchange substrate such as QAE-Sephadex® or GE cellulose. This method is unsuitable for large-scale commercial isolation of Hp because of the huge amounts of contaminated salt (ammonium sulphate) that would have to be disposed of. Batch methods of purification using an anion exchanger are also not ideal for scaling-up.

Isolation of Hp from sodium acetate-acetic acid precipitated rabbit plasma using the anion exchange substrate DE-52 microgranular cellulose (DEAE cellulose) has been reported (Basler and Burrel, 1983 Inflammation 7(4): 387-400). Preparative Isoelectric Focusing was necessary to achieve a reasonable degree of purity of the product. However, although a maximum yield of between 50 and 70% was quoted, analysis of the data indicates the yield was in fact 44% and the purification only three fold. This protocol is not suitable for use on a large commercial scale due to its complexity.

It is aim of the present invention to improve what is currently available for the isolation of Hp in one or more of the following respects: yield and/or purity of Hp and reproducibility thereof, simplicity of process and suitability for use on a large and/or commercial scale in terms of economic viability.

SUMMARY OF THE INVENTION

It has now been found that Hp can be isolated from a fraction of human plasma previously unknown as a source of Hp using an anion exchange substrate in a simple method which results in high, reproducible yields and which is capable of economic use on a large scale. Importantly, the isolation method is capable of being used in the purification of Hp for therapeutic uses (i.e. the final product is sufficiently pure and contaminant free for administration to humans).

The isolation of the components of human plasma is well documented. Methods for the isolation of proteins such as albumin and immunoglobulins have been known for many years. A common first step is the fractionation of the plasma. The most commonly used fractionation method is the Cohn method (Cohn, E. J. et al 1946 J. Am. Chem. Soc. 68: 459) and modifications thereof (e.g. Kistler and Nitschmann, 1962, Vox Sang, 7, p 414-24). This process begins with cryoprecipitation to remove some of the coagulation factors followed by celite treatment. The resultant plasma pool is treated with increasing concentrations of ethanol to precipitate fraction A+1 (a combination of fractions, I, II, and III) and fraction IV. Lowering the pH of the fraction IV supernatant and then dropping the temperature from −5 C (±1° C.) to −10° C. (±3° C.) causes the precipitation of Cohn fraction V.

Traditionally Cohn fraction V has been considered to be primarily a source of albumin. However, it has now been realised that Cohn fraction V is also a useful source of Hp and furthermore is a source from which Hp can be isolated successfully and with relative ease.

In a first aspect the present invention therefore provides a method for the isolation of haptoglobin from a sample comprising Cohn fraction V, wherein said method comprises anion exchange chromatography of said sample.

By "haptoglobin (Hp)" it is meant all phenotypes (including all isoforms) of Hp. The Hp isolated using the method of the invention will potentially contain all the isoforms of Hp present in the starting sample. The exact composition of the isolate will ultimately be dictated by the phenotypes of the source. Accordingly, if pooled plasma samples are used all isoforms will be isolated. A methodology has been devised for studying Hp polymorphism (Typing of haptoglobin using the Phastsystem, Hansson et al, Application Note 373 for the Phastsystem, Amersham Biosciences), and thus the skilled would be able to determine which isoforms are present in the isolate. The method can be used to determine which of the varying sizes of Hp isoforms are present. The use of haemogloblin to bind to haptoglobin and therefore provide a pseudoperoxidase activity that can be detected in a gel, can be substituted for western blotting with antibody detection (immunoblot).

We have discovered from using these techniques and others, for example high performance size exclusion chromatography (HPLC-SEC assay), Hp ELISA, Hb binding assay and turbimetric readings, that the different forms of Hp give differing signals in the different assays. For instance, the smaller molecular weight forms of Hp give a lower signal in the ELISA, and a higher signal by turbimetric analysis, than the larger molecular weight forms. The assays of choice for comparison of the quantities of the different forms are therefore western blots, HPLC-SEC and the Hb binding assay.

Different Hp isoforms are thought to have different biological effects as demonstrated from in-vitro observations and population studies in certain disease states. From a study of this data it is likely that the lower molecular weight forms isolated from fraction V will have a greater anti-inflammatory effect than the higher molecular weight forms. It is also clear from analysis of a different species of Hp that binding to human Hb may well be species specific. Knowledge of these differences has permitted optimisation of the fractionation method, and access to different Hp isoforms for in vitro investigations and in vivo efficacy studies.

By "isolation" it is meant that preferably at least 50% of Hp present in the fraction V starting sample is present in the product of the method of the invention. Preferably at least 65% and most preferably at least 80% of Hp present on the starting sample is present in the product of the method of the invention. The Hp obtained using the method of the invention will preferably be at least 70% pure, more preferably at least 80% pure and most preferably 90% pure. It should be noted that, like all isolation procedures, increases in purity are often associated with decreases in yield. Stages added to ensure viral safety may also lower the overall recovery.

The skilled man will be aware of techniques by which the purity/yield of an Hp isolate of the invention can be determined. These would include HPLC-SEC chromatography analysis (for samples that have a level of purity greater than 40%), a Hp-Hb binding assay (based on the method of Katnik et al, 1995, ibid) either in combination with the HPLC-SEC assay, when the sample is sufficiently pure, or spectrophotometry at A280 nm with an average extinction coefficient for plasma proteins, (Hansson et al, Application Note 373 for the Phastsystem, Amersham Biosciences). The specific activity of the product can also be determined using the Hb binding assay in combination with HPLC-SEC and the extinction coefficient as determined from the amino acid sequence.

By "Cohn fraction V" it is meant the plasma fraction designated Cohn fraction V in the Cohn fractionation method (Cohn, 1946, ibid) and any modification of said method, including the modified method of Kistler and Nitschmann (1962, ibid). The skilled man would readily understand which fraction is Cohn fraction V and would be able to prepare this fraction without undue burden. Briefly, this process can involve cryoprecipitation of plasma, celite treatment, then stepwise exposure to 19% ethanol at pH 5.85 and −5° C., 40% ethanol at pH 5.85 and −5° C. and finally 40% ethanol at pH 4.8 and −8° C., with precipitated material being removed at each stage. The final precipitate is Cohn fraction V. Any fractions equivalent in terms of composition to Cohn fraction V obtained in an alternative manner or known by an alternative terminology are considered to be encompassed by the invention. The main constituent of fraction V is albumin. Hp and transferrin are also present in appreciable amounts and alpha 1 acid glycoprotein can be detected at low levels. Trace amounts of other proteins are also present. The plasma may be obtained from any suitable biological source although plasma from mammalian blood is preferred. Most preferred is plasma from human blood.

By "sample comprising Cohn fraction V" it is meant that the majority of the proteinaceous component of the sample is Cohn fraction V. Preferably the only proteinaceous component of the sample is Cohn fraction V.

By "anion exchange chromatography" it is meant a method of chromatography by which separation is achieved on the basis of charge, specifically negative charge. Ion exchange chromatography utilises a charged solid support which binds molecules of a sample which is applied to the solid support. Unbound molecules may be the target molecules and thus the ion exchange step can be considered to be akin to a filtration step removing unwanted molecules. Alternatively the target molecules may be those which remain bound, the unbound molecules being unwanted. The latter is the more usual approach since elution of the bound molecules from the solid support can then be controlled/selective and thus a better quality of product can be achieved. Anion exchange chromatography techniques commonly use substrates such as, but not limited to, dextran, cellulose and modifications thereof that are positively charged. These substrates can comprise part of the solid support (e.g. a coating) or can form the entirety of the solid support. The solid support may be in particulate form (e.g. a resin) however non-particulate supports (e.g. filter papers or gels) may be used. Particulate substrates are typically, though not always, packed into columns.

When the term "substrate" or "anion exchange substrate" is used it should be interpreted to be referring to substrates in a form suitable for use in anion exchange techniques.

A sample which is to undergo anion exchange chromatography is applied to the substrate. On the basis of charge interactions, (negatively charged) molecules within the sample bind to the substrate. Washing of the substrate therefore removes unbound or weakly bound molecules. Controlled/selective elution of the bound molecules can be achieved by passing solutions of increasing salt concentration over the substrate since this disrupts the charge interactions between the substrate and the bound molecules. The pH of the elution solution may also be altered to induce elution since this will alter the charge present on the bound molecule and the substrate. The weaker the charge interaction between the molecule and the substrate, the lower the concentration of salt required to disrupt the interaction and thus induce the elution of that molecule from the substrate. By carefully controlling salt concentration, selective elution of bound molecules can be achieved.

The strength of the charge interaction can be modified by the choice of material for the solid support. For instance QAE-Sephadex® or GE cellulose are strong anion exchanger substrates whilst DEAE-cellulose and DEAE-Sephadex® are weak anion exchange substrates.

The skilled man will be well aware of anion exchange techniques and tools and would be able to devise and perform protocols specific to his needs. Of particular utility in the method of the invention are weak anion exchanger substrates and of exceptional utility is DEAE Sepharose® (Amersham). Sepharose® is the commonly used name for agarose beads. Other suitable anion exchange resins include cellulose, dextran and polymer based beads.

By "weak" it is meant anion exchanger substrates with a weak buffering capacity. The buffering capacity of any particular anion exchanger is readily determined by acid-base titration of the substrate, the resulting titration curve indicating the strength and breadth of the buffering capacity.

Thus, in a preferred embodiment the invention provides a method for the isolation of haptoglobin from a sample comprising Cohn fraction V wherein said method comprises anion exchange chromatography of said sample using a weak anion exchange substrate.

In a most preferred embodiment the invention provides a method for the isolation of haptoglobin from a sample comprising Cohn fraction V wherein said method comprises anion exchange chromatography using DEAE agarose.

Typically, the sample will be loaded onto the anion exchange substrate in a suitable loading solution. The anion exchange substrate and the loading conditions should be such that Hp is bound to the substrate whilst albumin, the major constituent of Cohn fraction V, remains unbound or is only weakly bound. The albumin may then be removed from the substrate using a suitable wash buffer, prior to selective elution of the Hp. For ease of processing, the anion exchange substrate is preferably in the form of a column. However, the method of the invention is not limited to column chromatography.

Also for ease of processing, the same components are preferably used in all the different buffers, with only the amounts or concentrations of the individual components varying between the different buffers.

Thus, in a preferred embodiment the invention provides a method for the isolation of haptoglobin from a sample comprising Cohn fraction V wherein said method comprises:
a) loading said sample onto an anion exchange substrate, and
b) selectively eluting haptoglobin therefrom.

One or more washing steps may also be included to reduce unwanted molecules in the Hp eluate. The object of a washing step is to pass a suitable buffer across the substrate which will elute unbound, or very weakly bound, molecules of the sample (e.g. albumin) without inducing the elution of the target molecule (Hp). Most commonly, one or more washing steps will be included between the step of loading the sample comprising Cohn fraction V onto the anion exchange substrate and the step of eluting Hp therefrom. However, washing steps may be included inbetween distinct elution steps, especially if other potentially useful molecules are to be eluted prior to the elution of Hp.

Highly preferably, the anion exchange substrate is washed to remove unbound material before the Hp is eluted therefrom.

Thus, in a preferred embodiment the invention provides a method for the isolation of haptoglobin from a sample comprising Cohn fraction V wherein said method comprises;
a) loading the sample onto an anion exchange substrate,
b) washing the substrate to remove unbound or weakly bound contaminants, and
c) selectively eluting Hp from the anion exchange substrate.

In another aspect, the invention provides a method for the isolation of albumin and haptoglobin from a sample comprising Cohn fraction V, the method comprising:
a) loading the sample onto an anion exchange substrate, followed by
b) washing the substrate to selectively remove albumin, and followed by
c) selectively eluting haptoglobin from the substrate.

The skilled man will be aware of suitable loading, washing and elution buffers and will be able to formulate suitable buffers (in terms of constituents and their concentrations and pH) to achieve either loading onto, washing of Hp bound to, or selective elution of Hp from the particular anion exchange substrate being used. The skilled man will be able to optimise these parameters without undue burden. The loading, washing and elution conditions should be selected such that no unnecessary damage to the Hp occurs. Typical loading, washing and elution buffers comprise a buffer component pair and a salt. Suitable buffer component pairs include, but are not limited to, sodium acetate and acetic acid, sodium citrate and citric acid, citric acid and sodium phosphate, and succinic acid and sodium hydroxide. A preferred buffer component pair is sodium acetate and acetic acid. Suitable salts include sodium chloride, potassium chloride, and sodium sulphate. A preferred salt is sodium chloride.

Since a wide variety of salts and buffer components can be used, the loading, washing and elution buffers can be alternatively defined in terms of their conductivity. The skilled man will be able to formulate buffers with any suitable salt and buffer component so long as the correct conductivity of the buffer is obtained. The skilled man would also appreciate that the conductivity required for each buffer type may depend on the anion exchange substrate used.

Loading and washing buffers are often the same. The following discussion of washing buffers is therefore applicable to loading buffers. However, the skilled man will be capable of devising separate loading and washing buffers from his common general knowledge should it be necessary.

For the washing of a weak anion exchange substrate to which Hp is bound without causing significant elution of Hp, a conductivity of between 0.1 and 3.0 mS/cm is preferred, more preferably the conductivity will be between 0.5 and 2.5 mS/cm and most preferably between 1.0 and 2.0 mS/cm.

For the washing of Hp bound DEAE Sepharose® without significant elution of Hp a conductivity of between 0.7 and 2.7 mS/cm is preferred, more preferably the conductivity will be between 1.1 and 2.3 mS/cm and most preferably between 1.2 and 2.2 mS/cm cm.

By way of example, a wash buffer with this most preferred conductivity comprises 5 mM sodium acetate and 15 mM sodium chloride adjusted to pH 4.6 with acetic acid.

For the elution of Hp from a weak anion exchange substrate a conductivity of between 8.0 and 15.0 mS/cm is preferred, more preferably the conductivity will be between 9.5 and 13.5 mS/cm and most preferably between 10.5 and 12.5 mS/cm.

For the elution of Hp from DEAE Sepharose® a conductivity of between 9.0 and 14.0 mS/cm is preferred, more preferably the conductivity will be between 10.0 and 13.0 mS/cm and most preferably between 10.5 and 12.5 mS/cm. By way of example, an elution buffer with this most preferred conductivity comprises 5 mM sodium acetate and 113.5 mM sodium chloride adjusted to pH 4.6 with acetic acid.

The pH of the loading, washing and elution buffers is also important. The pH may alter the conductivity of the buffer depending on the buffer constituents used and may also induce the elution (desired or not) of the target molecule from the substrate. In the case of washing buffers for the washing of Hp bound to a weak anion exchanger, a pH range of between 3 and 7 is preferred. More preferred is a pH of between 4 and 6 and most preferable is a pH of between 4.2 and 5.0. For a buffer comprising 5 mM sodium acetate and 15 mM sodium chloride at a conductivity of 1.7±0.5 mS/cm, the pH would be 4.6±0.1 (adjusted with acetic acid). In the case of elution of Hp from a weak anion exchanger a pH range of between 3 and 7 is preferred. More preferred is a pH of between 4 and 6 and most preferable is a pH of between 4.2 and 5.0. For a buffer comprising 5 mM sodium acetate and 113.5 mM sodium chloride at a conductivity of 11.5±1.0 mS/cm the pH would be 4.6±0.1 (adjusted with acetic acid). The skilled man will be aware of the relationship between pH and conductivity, and between pH and degree of elution, and will be able to predict precise pH ranges which are appropriate for the buffers and substrates being used and the function they are performing. Moreover, common general knowledge will enable optimisation of buffer parameters without undue burden.

In a most preferred embodiment the invention provides a method for the isolation of haptoglobin from a sample comprising Cohn fraction V wherein said method comprises;

a) applying said sample to a DEAE agarose anion exchange substrate, b) washing said substrate with a sodium acetate/acetic acid/sodium chloride washing buffer of a conductivity between 1.2 and 2.3 mS/cm and a pH of between 4.5 and 4.7, and c) eluting haptoglobin from said substrate with a sodium acetate/acetic acid/sodium chloride elution buffer of conductivity between 10.5 and 12.5 mS/cm and a pH of between 4.5 and 4.7

Depending on the other constituents present in the sample, it may be necessary to carry out step-wise elution to obtain Hp with a high degree of purity. Contaminants which bind to the substrate less strongly than Hp can be eluted first by suitable choice of initial elution conditions. Similarly, the elution buffer used to elute the Hp should be chosen such that it does not remove contaminants which bind to the substrate more strongly than does Hp. For example, albumin and transferrin bind to DEAE Sepharose more weakly than does Hp and are eluted before Hp. On the other hand, $\alpha 1$-acid glycoprotein (AAG) has been found to bind more strongly to DEAE Sepharose than does Hp and may remain bound to the column after Hp is eluted. In general, the more negatively charged a particular protein is, the more strongly it will bind to the anion exchange resin and the higher the salt concentration that is required to elute it will be. Any eluted proteins other than Hp may be discarded or, if they are potentially useful, they may be retained for further processing.

The skilled man will be aware of techniques for monitoring the eluate to enable the progress of the elution to be followed and to ascertain what is being eluted in the various fractions. For instance, UV spectroscopy can follow the progress of elution in real time. Techniques such as HPLC SEC chromatography or SDS PAGE can be used to detect the presence and identity of impurities. Matrix assisted laser desorption ionization time-of-flight (MALDI-ToF) mass spectrometry of HPLC fractions or SDS-PAGE bands can also be used to identify the proteins present. Known proteins can be monitored with antibody-based detection methods (e.g. enzyme-linked immunosorbent assay (ELISA), radial immuno diffusion (RID) and tubimetric determinations).

The method of the invention can also be used to achieve separation and isolation of particular isoforms of Hp. Separation can be achieved on the basis of charge. These differences in charge are likely to be a result of varying glycosylation patterns in the different isoforms. The lower the negative charge of an isoform, the lower the salt concentration required to elute that isoform. Typically salt concentrations increase during the course of the elution step and so the less negatively charged isoforms elute first. By monitoring the eluate in standard ways the skilled man would be able in the identify discrete peaks of elution which correspond to the discreet isoforms and accordingly isolate the discreet isoforms.

Thus, in another aspect the present invention provides a method for the isolation of individual haptoglobin isoforms from a sample comprising Cohn fraction V wherein said method comprises anion exchange chromatography of said sample.

The use of Cohn fraction V as the starting material may also have an affect on the isoforms of Hp that are ultimately isolated. It has been found that the proportions of the phenotypes of Hp present in fraction IV and fraction V of the Cohn fractionation process differ. Therefore, in isolating Hp from fraction V a different Hp product may be produced than the Hp product produced using fraction IV. Specifically, the proportion of the 1-1 isoform has been found to be greater than the proportion of 2-2 isoforms in the fraction V derived product when compared with a fraction IV derived product. This is postulated to be as a result of precipitation of the heavier isoforms as the pH is reduced at high ethanol concentration during the fractionation process.

Previously preferred embodiments of the invention apply mutatis mutandis to this aspect of the invention. When considering the term "isolation" in this aspect it must be borne in mind that any yield must be calculated with respect to the particular isoform.

A serious problem of prior art methods for the isolation of Hp from plasma has been their unsuitability for scaling up to large-scale/commercial isolation. As can be seen from the Examples, it has now been found that anion exchange chromatography can be used to achieve a high yield and high purity preparation of Hp from Cohn fraction V without the need for further processing steps such as Preparative Isoelectric Focusing. Thus the method of the invention is capable of being utilised on a large/commercial-scale and being economically viable at that scale.

By "large-scale" it is meant that isolation is achievable from volumes of starting sample in the order of thousands of liters. Viewed alternatively, large-scale refers to starting plasma batch sizes of at least 1000 liters, more preferably at least 3000 liters and most preferably at least 6000 liters.

Previously preferred embodiments of the invention apply mutatis mutandis to this aspect of the invention. The skilled man would be able to apply the previously discussed embodiments to large-scale production without undue burden.

Anion exchange chromatography can be used to isolate a significant proportion of the Hp in Cohn fraction V. The direct product of the anion exchange step of the method of the invention can be subjected to procedures to purify it further and/or concentrate the preparation. The skilled man would know of and be able to apply suitable procedures or devise alternatives. Examples of suitable procedures include, but are not limited to, diafiltration, ultrafiltration, flowthrough chromatography, metal chelate chromatography, hydroxyapatite chromatography, and dedicated virus inactivation/reduction procedures.

If the Hp is destined for pharmaceutical use, the isolated and/or purified Hp may need to undergo further processing to remove any biological or chemical contaminants that may remain in the sample. Such procedures are well known in the art and the skilled man would be able to apply his common general knowledge and perform routine testing to enable him to formulate the isolated/purified Hp to be suitable for pharmaceutical use.

For instance, one effective method of further purifying the Hp has been found to be by use of hydrophobic interaction chromatography (HIC) sorbents. Several HIC sorbents such as phenyl sepharose (high substituted, low substituted and high performance), butyl sepharose and octyl sepharose were investigated. In all cases, Hp was found to bind less strongly than the contaminants. The skilled person would be able to choose a HIC ligand suitable for his needs and would know that by modifying the ionic strength of the feed and equilibration buffers, molecules with different affinities for a HIC ligand could be collected in different fractions. For example, it may be preferred to choose conditions where the Hp flows through while the contaminants are bound, whilst in other situations the reverse may be true. The skilled man would also be aware of the factors that affect HIC purification such as pH and residence time. The residence time is especially critical in cases where the product is in the flowthrough. This is because shorter residence times may allow contaminants to flow through, thus contaminating the product.

Suitable HIC buffers have an ammonium sulphate concentration of between 0.5 M and 1.5 M, preferably between 0.8 M and 1.2 M and most preferably between 0.9 M and 1.1 M, and a pH of between 5 and 9, preferably between 6 and 8 and most preferably between 6.5 and 7.5. Suitable flow velocities for HIC would be no greater than 10 cm/min, preferably between 0.5 and 5 cm/min and most preferably between 1 and 3 cm/min.

Diafiltration may be used to adjust the salt concentration or pH to be suitable for pharmaceutical use. Biological contaminants such as viruses or prions can be removed by known virus filtration techniques, by known chemical disinfection (viral inactivation) techniques and/or by known pasteurisation or heat treatment techniques. For example, we have found that large scale virus removal and/or inactivation of a solution containing Hp is possible using solvent detergent treatment as outlined in EP-A 0131740, providing the Hp is treated at a pH in the range pH 5-9. It is also possible to filter the Hp produced by the purification methods described herein through one or more suitable virus filters, for example filters with pore sizes of about 20 nm, and thus theoretically ensure removal of potentially pathogenic viruses. If solvent detergent treatment is used to inactivate viruses a further step may be included in the method to remove the solvent detergent reagents. The skilled man would be familiar with such methods. By way of example, anion exchange chromatography may be used. A suitable anion exchange chromatography step would be the same as those discussed herein in relation to the initial purification of Hp. More specifically, a solvent detergent reagent removal step could comprise diluting the solvent detergent treated sample appropriately to keep conductivity below 3 mS/cm, loading the treated sample onto an anion exchange substrate (for example a DEAE agarose substrate), washing the substrate to selectively remove unbound or weakly bound contaminants, and selectively eluting Hp from the anion exchange substrate. Use of anion exchange chromatography for the removal of the solvent detergent reagents may also lead to improved purity of the final product.

If pasteurisation or heat treatment is used the use of stabilisers is contemplated. Stabilisers would include, but are not limited to, sugars, sugar alcohols, ascorbic acid and amino acids. Methods to remove stabilisers, if necessary, are well known in the art. If a chemical disinfectant (e.g. solvent/detergent) is used this is also likely to need removal. Methods for removal of chemical disinfectants are well known in the art. The particular order of the above mentioned procedures is not considered important, however particular orders may be more advantageous than others in terms of expediency and cost. For instance, it may be preferable to perform pasteurisation with stabilisers or perform a chemical disinfection step prior to a filtration or dialysis step that could be designed to remove the stabilisers or disinfection agent. Blood products for use as pharmaceuticals will preferably undergo at least two viral inactivation steps. The Hp may be subsequently formulated for clinical use.

In a formulation of Hp suitable for pharmaceutical use, Hp should be substantially free of chemical and biological contaminants, to the extent that the levels in the formulation would not be considered harmful to a patient. Ideally, the levels of any contaminants will be substantially lower than the minimum levels required by Regulatory bodies in relation to pharmaceuticals.

By "biological contaminants" it is meant biological entities capable of inducing pathologies in a patient. Such entities include, but are not limited to, viruses, prions, bacteria, fungi, spores, and cells.

By "chemical contaminants" it is meant molecules that would induce adverse reactions if administered to patients.

In a still further aspect the invention provides products obtained by any and all methods of the invention hereinbefore described.

BRIEF DESCRIPTION OF THE DRAWINGS

Any and all combinations of preferred features discussed herein are encompassed by the invention even if not explicitly disclosed. The invention will be further described with reference to the following Figures in which:

FIG. 2 shows the HPLC analysis of the Hp peaks (peak 1 and peak 2) for Hapto011.

FIG. 4 shows the HPLC analysis of the Hp peaks (peak 1 and peak 2) for Production Run.

DETAILED DESCRIPTION OF THE INVENTION

Example 1

Preparation of Cohn Fraction V

Figure 1:
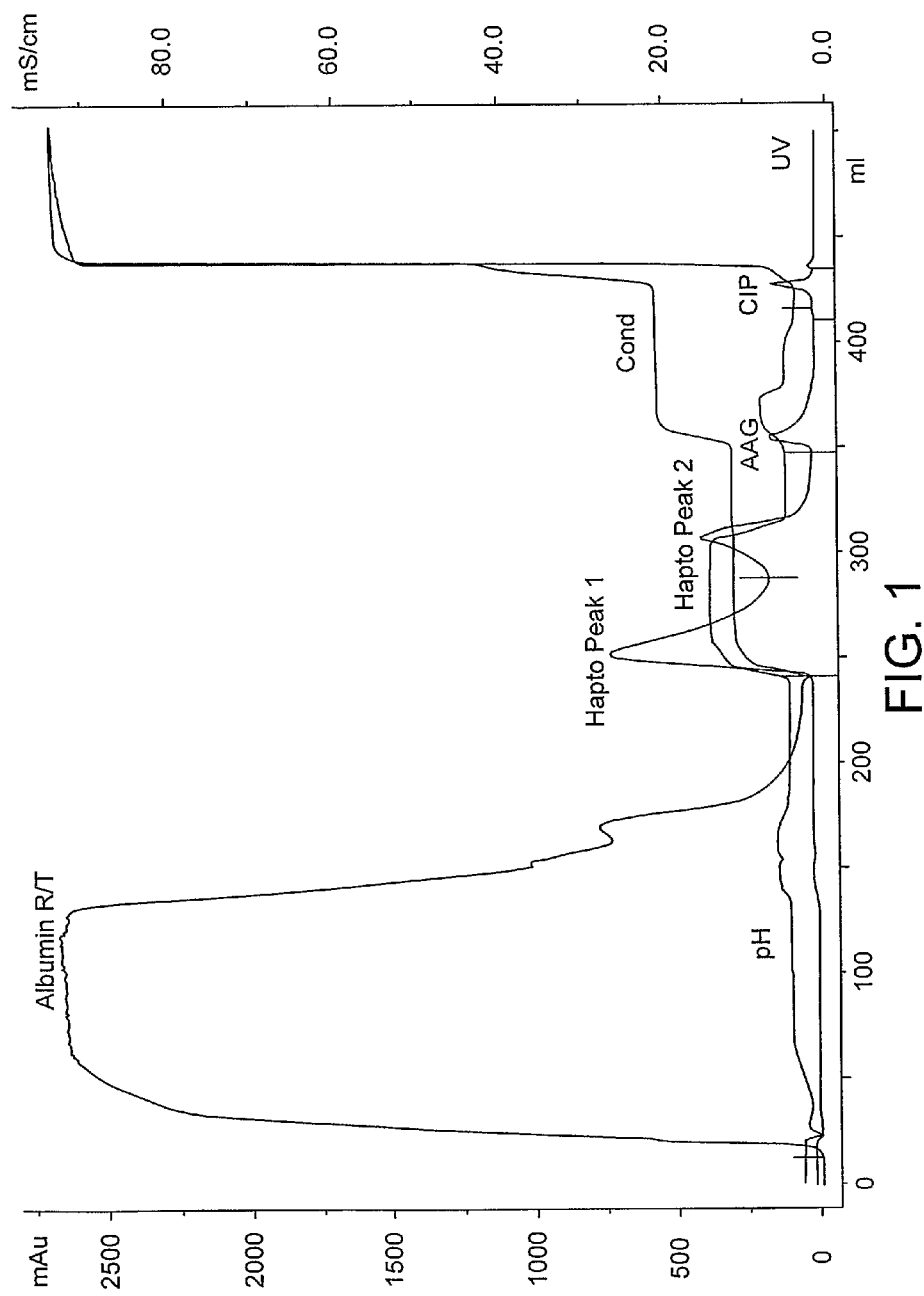
FIG. 1 shows results from an example of laboratory scale Hp isolation experiment. The three traces correspond to conductivity (Cond), pH (pH), and UV absorbance (UV). Peaks of protein elution are marked albumin R/T, Hapto peak 1, Hapto peak 2 and AAG (al-acid glycoprotein).

Plasma was subjected to a controlled thaw at −0.5° C. to 2° C. during which some proteins precipitated. The supernatant was collected, treated with celite and then filtered to remove other unwanted proteins. The resulting supernatant was adjusted to a pH of 5.85 with acetate buffer and 17-21% ethanol v/v was added. The temperature was controlled during the ensuing precipitation at between −4° C. and −6° C. These conditions are similar to those used in the second stage of the Kistler and Nitschmann process and so the precipitate includes fraction 1 and precipitate A of that process. The precipitate is referred to as A+1. The supernatant was further fractionated by the adjustment of ethanol concentration to between 38 and 42%. The precipitated proteins are known collectively as fraction IV in the Kistler and Nitschmann process. Adjustment of the pH to 4.85 and the temperature to between −7° C. and −13° caused fraction V to precipitate.

Example 2

Anion Exchange Columns and Preparation of Buffers and Solutions

Columns:
 Examples 1 and 2, DEAE Sepharose® (Amersham) 12.5 cm bed height in an Amersham 16/20 XK column.
 Examples 3 and 4, commercial-scale DEAE Sepharose® (Amersham) column
Equilibration/Wash Buffer:
 5 mM sodium acetate, analar (0.68 g/l of sodium acetate trihydrate)
 15 mM sodium chloride, analar (0.88 g/l)
 prepared in Pyrogen Free Water (PFW)
 pH: 4.6±0.1 (pH adjusted with glacial acetic acid, analar)
 Conductivity: 1.7±0.5 mS/cm
 For 400 liters of equilibration/wash buffer, 272 g sodium acetate trihydrate, 351 g sodium chloride, and 110 g glacial acetic acid were added to a suitable (at least 500 l capacity) vessel. The ingredients were dissolved and made up to 400 l with suitable water. pH and conductivity readings were checked. Acceptance range pH 4.5-4.7. Conductivity: 1-2 mS/cm
Hp Elution Buffer:
 5 mM sodium acetate, analar (0.68 g/l of sodium acetate trihydrate).
 113.5 mM sodium chloride (6.63 g/l)
 pH: 4.6±0.1
 Conductivity: 11.5±1 mS/cm
 For 500 liters of elution buffer, 340 g of sodium acetate trihydrate, 3.32 kg of sodium chloride and 110 g of glacial acetic acid were added to a suitable (at least 500 l capacity) vessel. The ingredients were dissolved and made up to 500 l with suitable water. pH and conductivity readings were checked. Acceptance range pH 4.5-4.7. Conductivity: 10.5-12.5 mS/cm
AAG Elution Buffer
 5 mM sodium acetate, analar (0.68 g/l of sodium acetate trihydrate).
 212 mM sodium chloride (12.40 g/l)
 pH: 4.6±0.1
 Conductivity: 19.5±2.5 mS/cm
 For 400 liters of AAG Elution Buffer, 272 g of sodium acetate trihydrate, 4.96 kg of sodium chloride and 110 g of glacial acetic acid were added to a suitable (at least 500 l capacity) vessel. The ingredients were dissolved and made up to 400 l with suitable water. pH and conductivity readings were checked. Acceptance range pH 4.5-4.7. Conductivity: 17-22 mS/cm Example 3

Laboratory Scale Isolation of Hp

Isolation of Hp from Cohn fraction V was performed on a laboratory scale. Anion exchange substrate DEAE-Sepharose® Fast Flow was packed to a bed height of 12.5 cm in a 25 ml column housed in an Amersham BioSciences 16/20 XK column. This is a scale-down version (1/4000) of a commercial-scale column.

Cohn fraction V solution was loaded onto the column. The Cohn fraction V load was reduced from 250 ml to 150 ml to save processing time. After loading was completed the column was washed with equilibrium buffer. Albumin eluted in the flowthrough of the load. Elution of Hp was then induced by running elution buffer through the column. Flow rate of the buffers was maintained at 4.0 ml/min throughout the entire process. FIG. 1 shows the presence of protein in the eluate as monitored by UV absorbance as a function of the volume of the buffer run through the column. The conductivity and pH of the eluate are also shown. As can be seen, Hp eluted as two peaks after albumin was eluted.

Figure 2A:
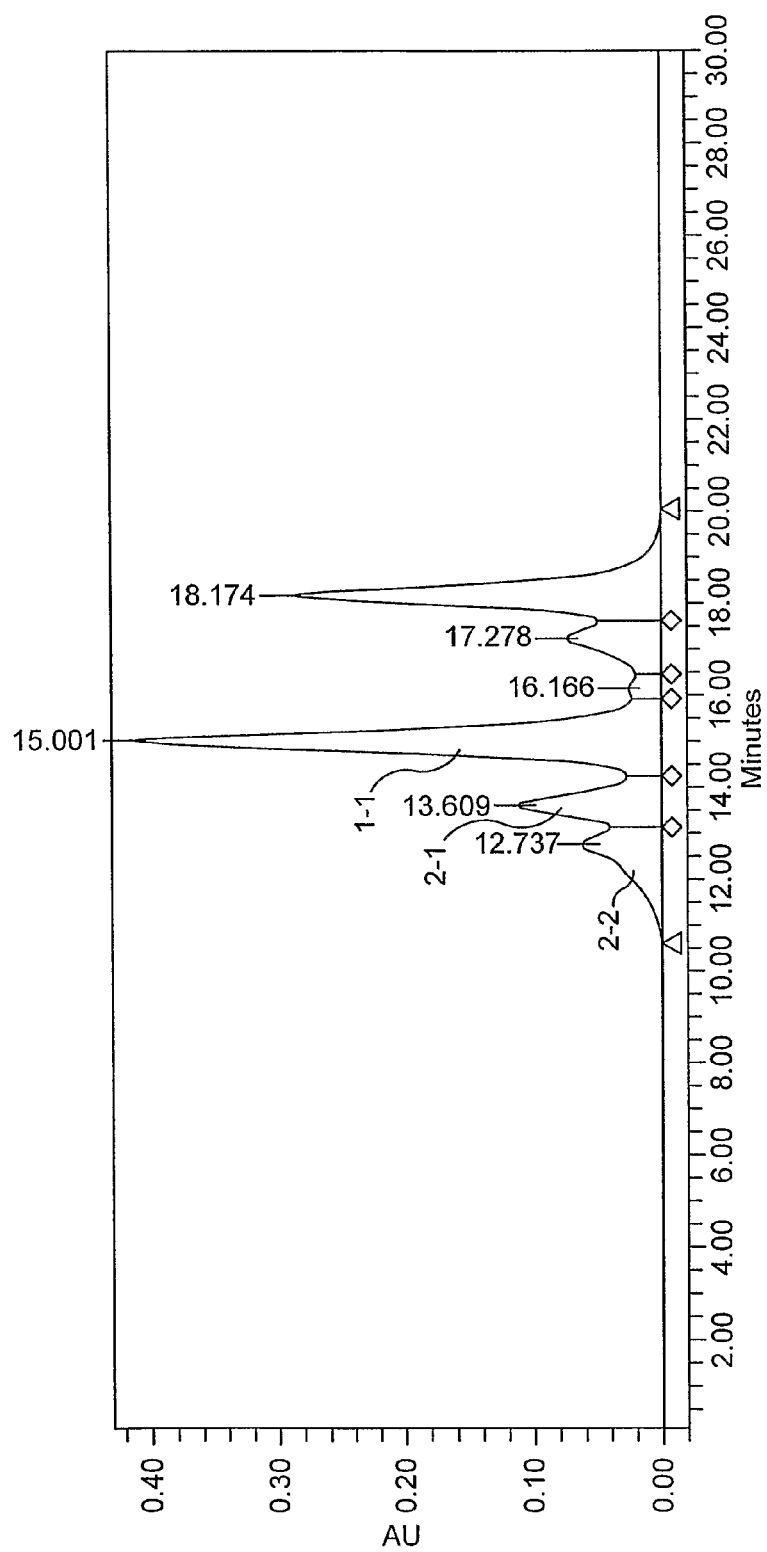
FIG. 2a, peak 1.
Figure 2B:
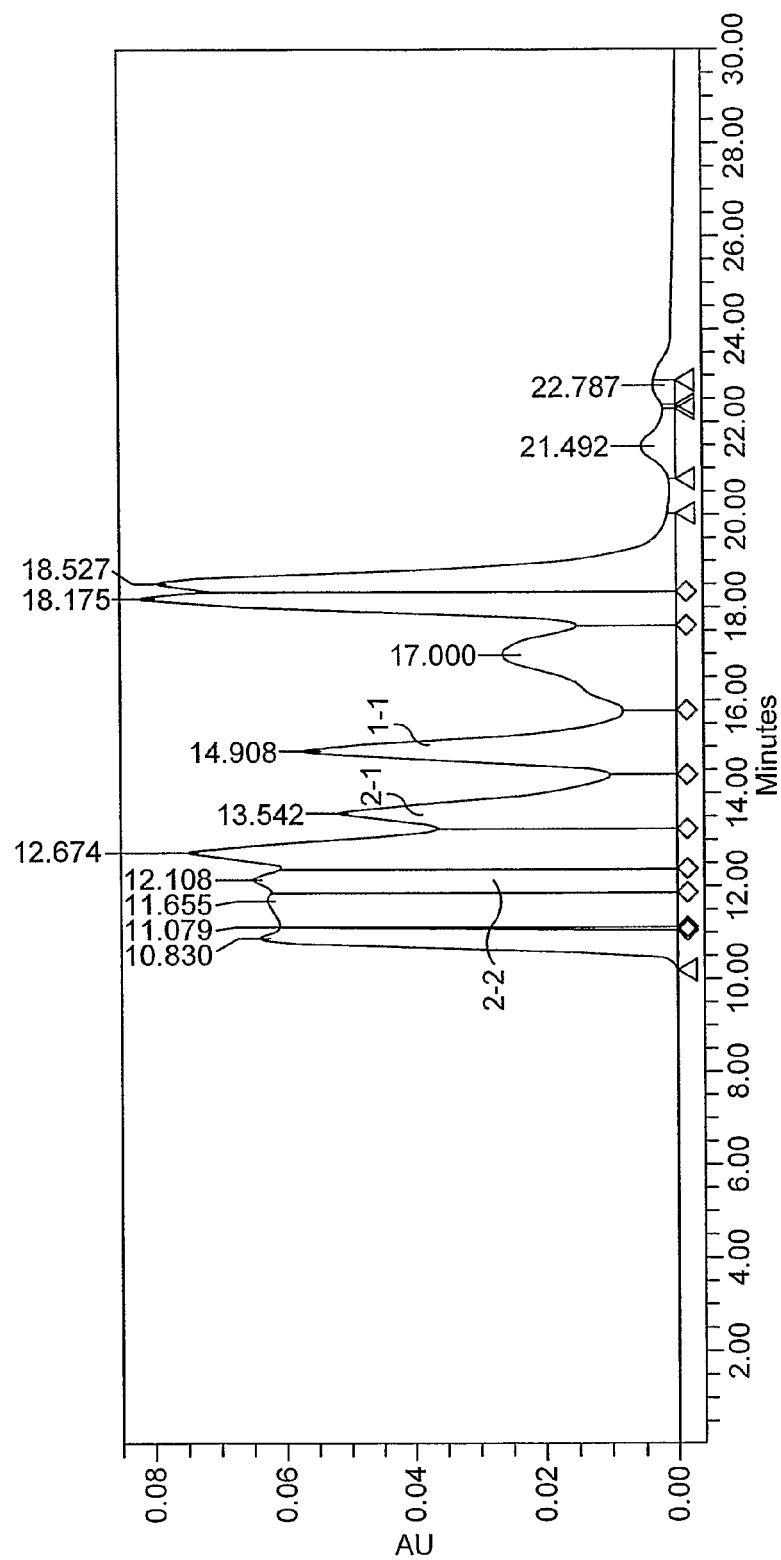
FIG. 2b, peak 2.

The samples corresponding to the two Hp peaks were further analysed by HPLC. FIG. 2 shows that Peak 1 (FIG. 2a) had more Hp 1-1 than the other forms and that Peak 2 (FIG. 2b) was richer in the higher Hp forms (Hp 2-2 and 2-1) than Peak 1. In this example, for peak 1, the purification factor was 40 fold, the purity 72% and the yield 80%. Peak 2 had a purity of 40%.

Example 4

Large Scale Isolation of Hp

Figure 3:
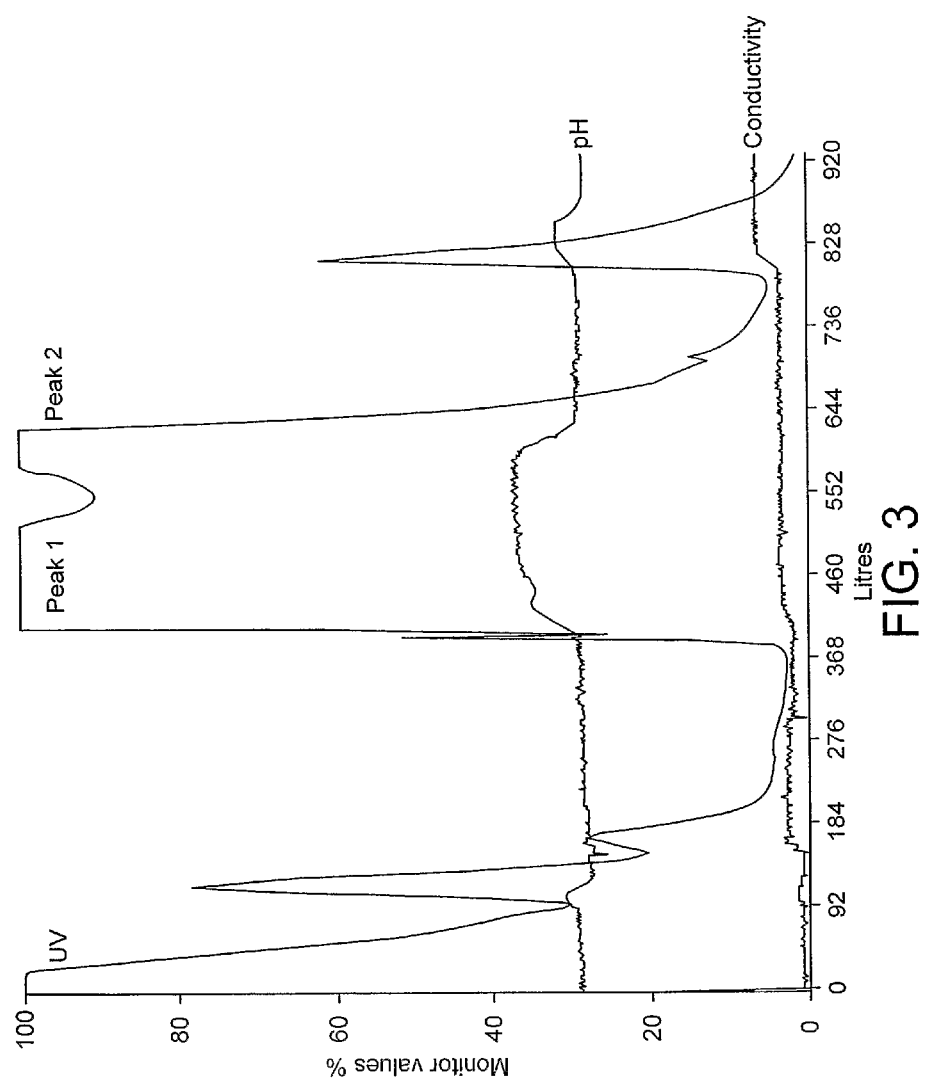
FIG. 3 shows results from an example of commercial scale Hp isolation experiment (Production Run). The three traces correspond to conductivity (Cond), pH (pH), and UV absorbance (UV).

Isolation of Hp from Cohn fraction V was performed on a commercial scale using a DEAE-Sepharose® column at full production scale (100 liter column). Cohn fraction V solution (1100 liters) was loaded onto the column. Once loading was completed the column was washed with washing buffer. This caused the albumin to be eluted. Hp was then eluted with elution buffer. Flow rate of the buffers was maintained at 14 liters/min, which is equivalent to 4.0 ml/min at the laboratory scale. FIG. 3 shows the presence of protein in the eluate (monitored by UV absorbance) as a function of the volume of the buffer running through the column. The chromatogram begins at the end of the albumin elution peak. As can be seen Hp eluted as two peaks after albumin was eluted. The similarity of this trace compared with the laboratory scale experiment highlighted the suitability of the method of the invention for scale up for commercial isolation of Hp.

Figure 4A:
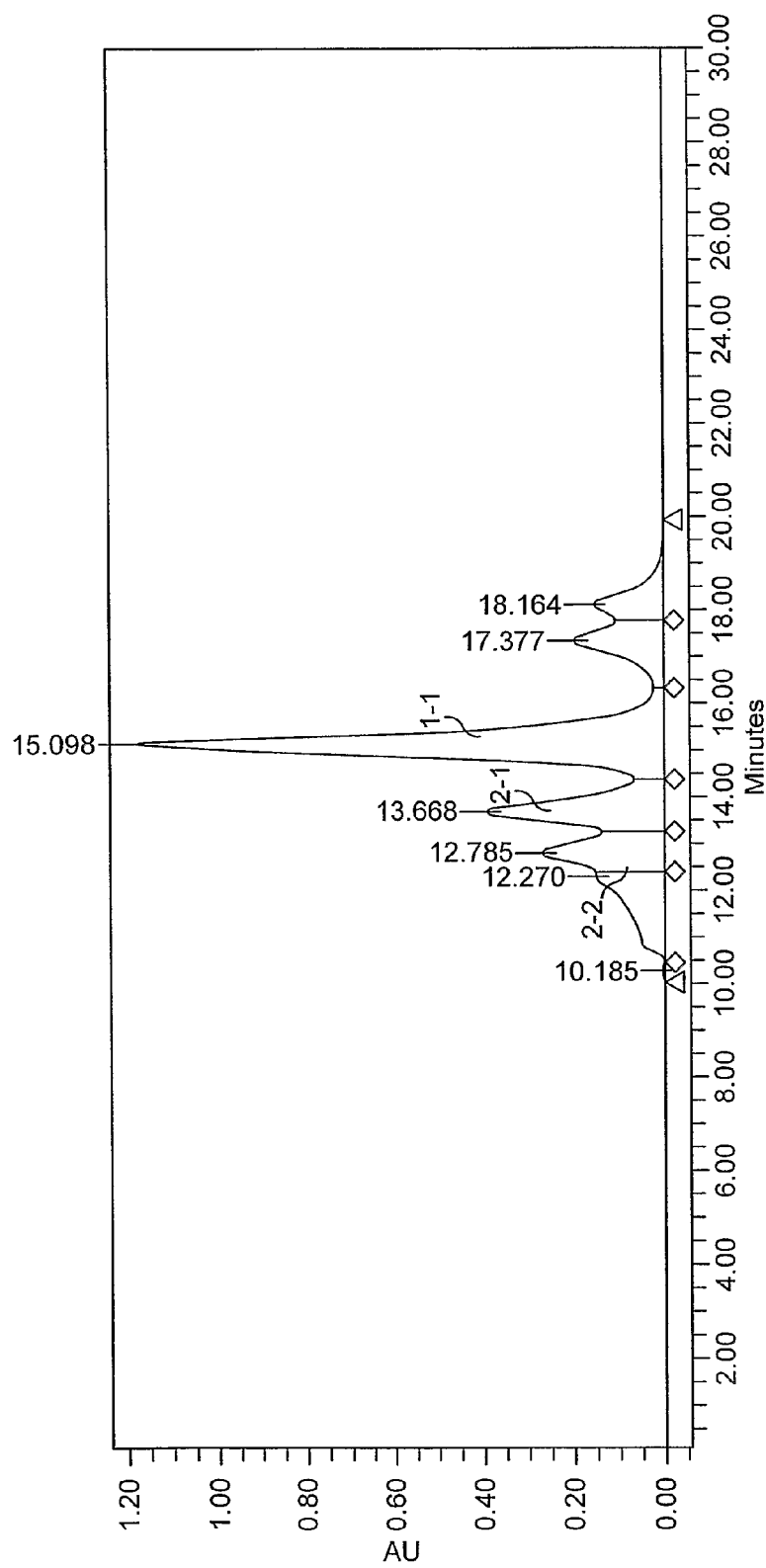
FIG. 4a, peak 1.
Figure 4B:
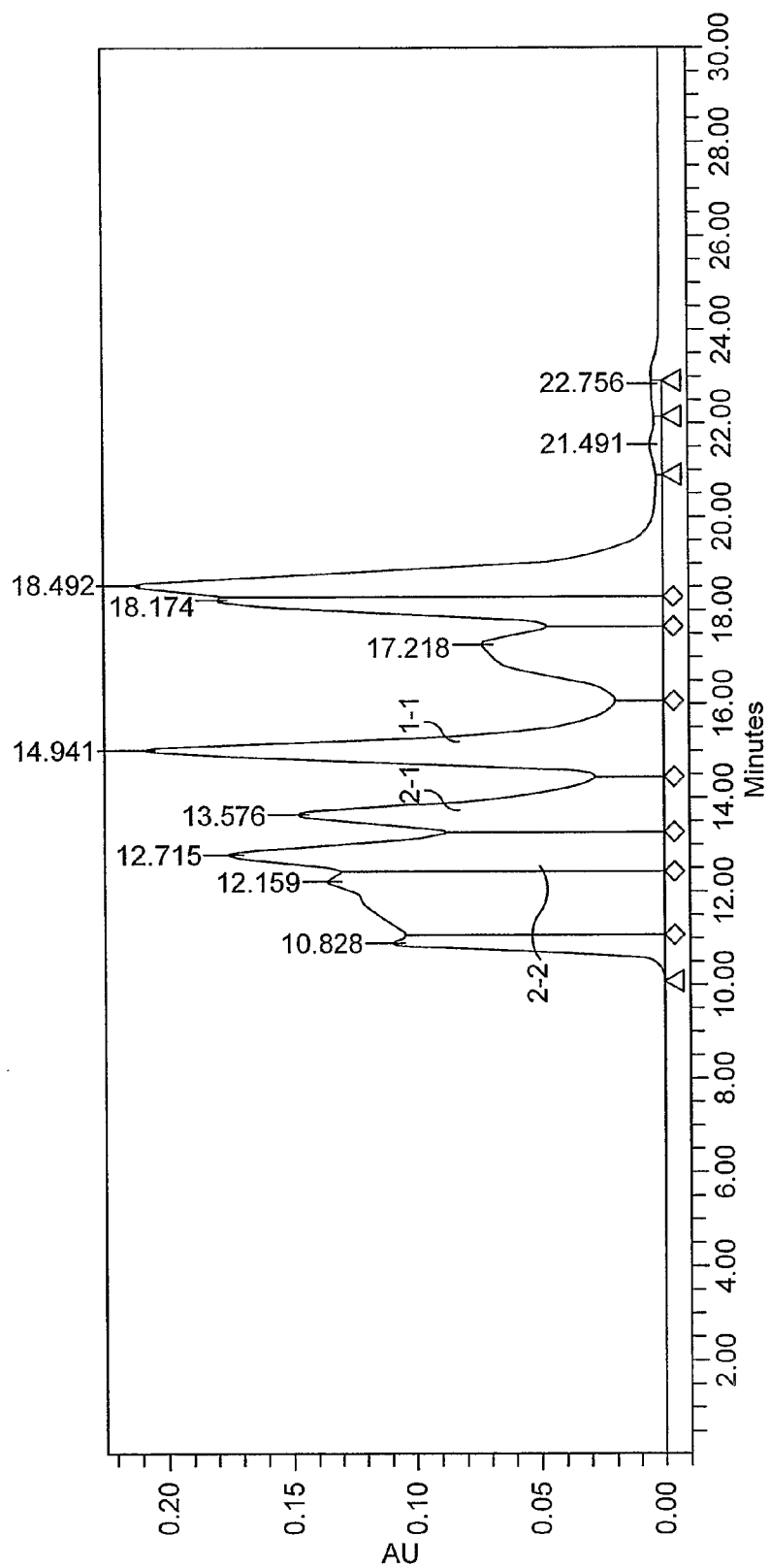
FIG. 4b, peak 2

The samples corresponding to the two Hp peaks were further analysed by HPLC. FIG. 4 shows that Peak 1 (FIG. 4*a*) had more Hp 1-1 than the other forms and that Peak 2 (FIG. 4*b*) was richer in the higher Hp forms (Hp 2-2 and 2-1) than Peak 1. The purity of peak 1 was 67%, that of peak 2 was lower. The yield of peak 1 was approximately 74%. As only a sample of peak two was taken, the yield of this peak could not be assessed. In addition, by comparing the Production analytical results with the analytical results, it can be seen that scale-up does not affect the quality of the product.

Example 5

Hp Purification on Butyl Sepharose

The Hp fraction obtained from Example 4 (peak 1) was further purified on butyl sepharose. A prepacked 20 ml HiPrep™ Butyl ff was equilibrated with 180 ml of 1.0 M ammonium sulphate in 50 mM $Na_2HPO_4$ buffer pH 7.0 at a flow rate of 4.5 ml/min (135 cm/h). 40 ml of peak 1 from Example 4 was then loaded at 3.5 ml/min. The column was then washed with 20 ml of the equilibration buffer. The flowthrough and the wash (haptoglobin product) were collected in one vessel. Bound molecules (contaminants) were washed off the column with de-ionised water. The flowthrough (Hp) was analysed by HPLC-SEC. From the areas of the peaks, 98% of total protein was Hp and 67% was Hp having a molecular weight of about 100 kDa.

Analogous experiments were performed using high substituted, low substituted and high performance phenyl sepharose and octyl sepharose columns. High substitution phenyl sepharose gave a purity of 99% and a yield of 32%. The remaining sorbents gave purities of between 96% and 97% and yields of between 32% and 61%.

Optimisation experiments using HiPrep™ Butyl ff have shown that a) the pH should be between 6 and 8, b) the ammonium sulphate concentration should be between 0.8M and 1.2M, c) the loading flow rate should be between 1 and 3 cm/min.

Example 6

Hp Stability

The Hp produced by the methods of the invention has been shown to be resilient to a wide range of pH conditions making further purification schemes requiring acid or alkaline conditions feasible. In one example, 3 ml of Hp from peak 1 in Example 4 was incubated with 3 ml of buffer (200 mM glycine for pH 2, 3, and 4, 200 mM $NH_4HCO_3$ for pH 11). Samples were taken at 0, 4, 7, 24, 48 and 72 hr. Samples were immediately neutralised with 1 M Tris-HCl pH 7.0. The samples were then analysed by silver stained SDS-PAGE and the results of the analysis showed that Hp can withstand a pH range of 4-11 for 72 hours. However, at pH 2 complete aggregation occurred within 4 hours and at pH 3 partial degradation was observed (as evidenced by extra bands on the SDS-PAGE).

It has also been shown that the Hp produced by the methods of the invention is stable at 4° C. for periods in excess of 18 months without the addition of any protein, monosaccharide or disaccharide excipient. Extreme temperatures, specifically those above 40° C., produce Hp aggregation after a short or longer period, depending on temperature. For example, incubation of Hp at 60° C. for 24 hrs resulted in complete aggregation as shown by HPLC-SEC.

Example 7

Solvent Detergent Treatment of Hp

Peak 1 from Example 4 was solvent detergent treated following the method of patent number EP-A 0131740. Briefly, 4.32 g of polysorbate 20, 1.16 g of tri n-butylphosphate (TnBP) and 14.52 g of WFI (water for injection) were mixed vigorously for 15 minutes. 8.7 g of this mixture was added to 150 ml of peak 1 from Example 4 and incubated at 25° C. for 30 minutes. The sample was then diluted to 475 ml with WFI. The diluted sample was then loaded on to a 30 ml DEAE column with buffers as used in Example 3. Unbound molecules and the solvent detergent (SD) reagents were washed off the column. Hp was eluted as in Example 3. The Hp obtained was analysed by a) SDS-PAGE which showed that most of the contaminants were removed, and by b) haemoglobin binding assay which showed that 63% of active Hp was recovered in the product. The remaining 37% was lost during the washing step thus showing that the SD treatment does not affect the activity of the Hp.

It is also possible to filter the Hp produced by the purification methods described herein through one or more 20 nm virus filter(s) thus theoretically ensuring removal of potentially pathogenic viruses including non enveloped viruses, that may not have been inactivated by the SD treatment.

What is claimed is:

1. A method for isolation of human haptoglobin (Hp) from human Cohn fraction V, comprising the steps of:
    a) providing human Cohn fraction V,
    b) loading said human Cohn fraction V directly onto a weak anion exchange substrate in a loading buffer of a conductivity between 0.1 mS/cm and 3.0 mS/cm and a pH of 4 to 5, wherein human Hp binds to the weak anion exchange substrate, and
    c) selectively eluting human Hp from the weak anion exchange substrate.

2. The method as claimed in claim 1 wherein all isoforms of human Hp present in the human Cohn fraction V are isolated from the human Cohn fraction V.

3. The method as claimed in claim 1 wherein said method comprises anion exchange chromatography of said human Cohn fraction V.

4. The method as claimed in claim 3 wherein said weak anion exchange substrate is DEAE agarose.

5. The method as claimed in claim 1 wherein said method further comprises after step (b) and before step (c): washing the weak anion exchange substrate to remove unbound or weakly bound contaminants.

6. The method as claimed in claim 5 wherein the washing step use a buffer of conductivity between 0.1 and 3.0 mS/cm.

7. The method as claimed in claim 6 wherein the washing step use a buffer of conductivity between 1.0 and 2.0 mS/cm.

8. The method as claimed in claim 5 wherein the loading and washing steps use buffers of pH between 4.2 and 5.0.

9. The method as claimed in claim 1 wherein the elution step uses a buffer of conductivity of between 8.0 and 15.0 mS/cm.

10. The method as claimed in claim 9 wherein the elution step uses a buffer of conductivity between 10.5 and 12.5 mS/cm.

11. The method as claimed in claim 1 wherein the elution step uses buffers of pH between 4 and 6.

12. The method as claimed in claim 11 wherein the elution step uses a buffer of pH between 4.2 and 5.0.

13. The method as claimed in claim 1 wherein loading and/or elution buffers comprise sodium acetate, acetic acid and sodium chloride.

14. The method as claimed in claim 1 wherein said step (c) comprises eluting human Hp from said weak anion exchange substrate with a sodium acetate/acetic acid/sodium chloride elution buffer of conductivity between 10.5 and 12.5 mS/cm and a pH of between 4.5 and 4.7, and wherein, between step (b) and (c), said method further comprises washing said weak anion exchange substrate with a sodium acetate/acetic acid/sodium chloride washing buffer of a conductivity between 1.2 and 2.3 mS/cm and a pH of between 4.5 and 4.7.

15. The method as claimed in claim 1 further comprising monitoring an eluate to identify elution of discrete human Hp isoforms.

16. The method as claimed in claim 15 wherein human Hp1-1 isoform is preserved in the final product.

17. The method as claimed in claim 1 wherein said method further comprises at least one concentration and/or purification step.

18. The method as claimed in claim 17 wherein the at least one purification step is hydrophobic interaction chromatography.

19. The method as claimed in claim 1 wherein said method further comprises at least one contaminant removal step.

20. The method as claimed in claim 19 wherein said contaminant removal step is a virus inactivation or removal step.

21. The method as claimed in claim 20 wherein said virus inactivation or removal step comprises solvent detergent treatment and/or virus filtration.

22. The method as claimed in claim 1 further comprising:
(d) treating the eluted human Hp of step (c) by solvent detergent for virus inactivation and chromatographically removing the solvent detergent reagents;
(e) removing viruses from the human Hp of (d) by filtration; and
(f) formulating the human Hp in a physiological buffer;
wherein step (d) and step (e) may be performed in either order.

23. The method as claimed in claim 5 wherein washing further comprises contacting said weak anion exchange substrate with a washing buffer comprising sodium acetate, acetic acid and sodium chloride.

24. The method as claimed in claim 17 wherein the at least one concentration and/or purification step is selected from the group consisting of diafiltration, ultrafiltration, flowthrough chromatography, metal chelate chromatography and hydroxyapatite chromatography.

25. The method as claimed in claim 19 wherein said contaminant removal step is a step to remove a biological contaminant by pasteurization or heat treatment, and wherein said pasteurization or heat treatment is performed in the presence of stabilizers selected from the group consisting of sugars, sugar alcohols, ascorbic acid and amino acids.

* * * * *